United States Patent
Elman et al.

(10) Patent No.: US 6,900,324 B2
(45) Date of Patent: May 31, 2005

(54) PROCESS FOR PREPARING A SUBSTITUTED IMIDAZOPYRIDINE COMPOUND

(75) Inventors: Björn Elman, Märsta (SE); Silke Erbeck, Kölliken (CH); Eric Thiemermann, Fribourg (CH)

(73) Assignee: AstraZeneca AB, Sodertalje (SE)

( * ) Notice: Subject to any disclaimer, the term of this patent is extended or adjusted under 35 U.S.C. 154(b) by 41 days.

(21) Appl. No.: 10/363,806

(22) PCT Filed: Sep. 5, 2001

(86) PCT No.: PCT/SE01/01897

§ 371 (c)(1),
(2), (4) Date: Jun. 27, 2003

(87) PCT Pub. No.: WO02/20523

PCT Pub. Date: Mar. 14, 2002

(65) Prior Publication Data

US 2004/0039013 A1 Feb. 26, 2004

(30) Foreign Application Priority Data

Sep. 7, 2000 (SE) ............................. 00031864

(51) Int. Cl.$^7$ ............................................. C07D 471/04
(52) U.S. Cl. ...................................................... 546/121
(58) Field of Search ......................................... 546/121

(56) References Cited

U.S. PATENT DOCUMENTS

| | | | |
|---|---|---|---|
| 4,450,164 A | 5/1984 | Bristol et al. | 424/256 |
| 4,725,601 A | 2/1988 | Ueda et al. | 514/300 |
| 4,782,055 A | 11/1988 | Ueda et al. | 514/241 |
| 4,920,129 A | 4/1990 | Shiokawa et al. | 514/300 |
| 6,245,818 B1 | 6/2001 | Lignell | 514/691 |
| 6,313,137 B1 | 11/2001 | Amin et al. | 514/300 |

*Primary Examiner*—Johann Richter
*Assistant Examiner*—Ebenezer Sackey
(74) *Attorney, Agent, or Firm*—White & Case LLP

(57) ABSTRACT

The present invention provides a new process for large-scale preparation of substituted imidazopyridine compound of formula (1) wherein $R^1$ is $C_1$–$C_6$ alkoxy or $NH_2$ group, comprising the step of reacting a compound of formula (2) with a 3-halo-2-butanone compound in cyclohexanone.

10 Claims, No Drawings

PROCESS FOR PREPARING A SUBSTITUTED IMIDAZOPYRIDINE COMPOUND

FIELD OF THE INVENTION

The present invention relates to a new process for the preparation of a substituted imidazopyridine compound, more specifically a new process for the preparation of a 2,3-dimethylimidazo[1,2-a]pyridine substituted in the 6-position by a carboxamido or a carboxyalkyl group. In further aspects, the present invention also relates to new intermediates used in the process.

BACKGROUND AND PRIOR ART

The present invention relates to a new process suitable for large-scale preparation of a substituted imidazopyridine compound of formula (1),

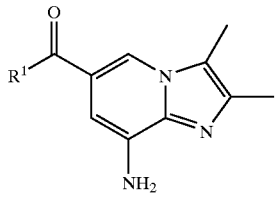
(1)

wherein $R^1$ is a $C_1$–$C_6$ alkoxy or $NH_2$ group, comprising the step of reacting a compound of the formula (2)

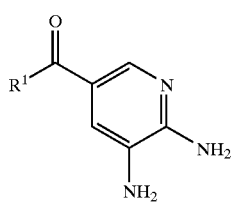
(2)

wherein $R^1$ is a $C_1$–$C_6$ alkoxy or $NH_2$ group, with a 3-halo-2-butanone compound in cyclohexanone.

A similar reaction is described in EP 33094, EP 204 285, EP 228 006, EP 308 917, and WO 99/55706 wherein a substituted aminopyridine compound of the general formula (X)

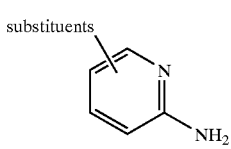
(X)

is reacted with a compound of formula

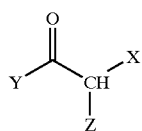

wherein
X is i.a. H, $CH_3$ or an ester group, such as $COOCH_3$ or $COOC_2H_5$,
Y is i.a. $CH_3$, $CH_2CH_3$, and
Z is a leaving group, such as halogen, mesyl or tosyl, to give a compound of the general structure

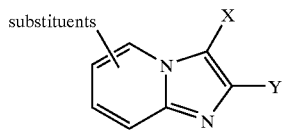

wherein X and Y are as described above.

The reaction is carried out in an inert solvent, such as acetone, alcohols, benzene, N,N-dimethylformamide, tetrahydrofurane, chloroform, or diethyl ether, preferably at elevated temperature, and optionally in the presence of an inorganic or organic base.

The reaction is characterized by long reaction times, e.g. 16 to 84 hours, high reaction temperatures and relatively low yields, e.g. 22% to 55%. The reaction is thereby not suitable for large-scale preparation of substituted imidazopyridine compounds.

We have surprisingly found that if the process of the present invention is carried out as described herein the reaction time can be shortened, the reaction temperature can be lowered and the yield is increased.

OUTLINE OF THE INVENTION

The present invention provides a new process for large-scale preparation of substituted imidazopyridine compound of formula (1)

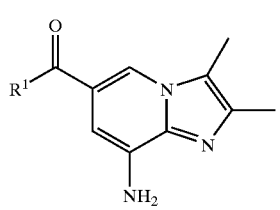
(1)

wherein $R^1$ is a $C_1$–$C_6$ alkoxy or $NH_2$ group, comprising the step of reacting a compound of the formula (2)

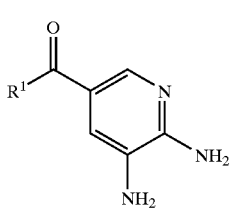
(2)

with a 3-halo-2-butanone compound in cyclohexanone.

In a first embodiment of the present invention a compound of the formula (2)

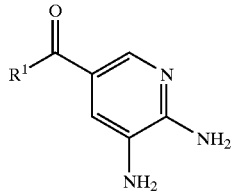

(2)

wherein $R^1$ is a $C_1$–$C_6$ alkoxy group, is reacted with a 3-halo-2-butanone compound in cyclohexanone to give a compound of the formula (1)

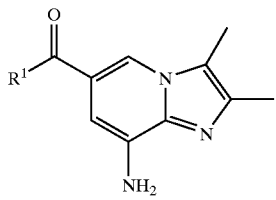

(1)

wherein $R^1$ is a $C_1$–$C_6$ alkoxy group.

In a second embodiment of the present invention a compound of the formula (2)

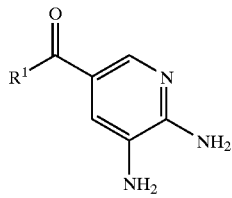

(2)

wherein $R^1$ is a $NH_2$ group, is reacted with a 3-halo-2-butanone compound in cyclohexanone to give a compound of the formula (1)

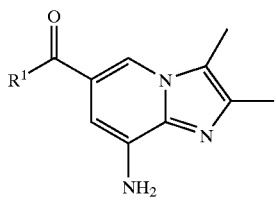

(1)

wherein $R^1$ is $NH_2$ group.

The process of the present invention is performed by solving or suspending a compound of formula (2)

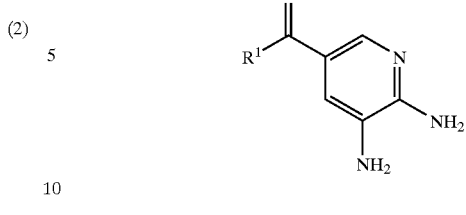

(2)

wherein $R^1$ is a $C_1$–$C_6$ alkoxy or $NH_2$ group, in cyclohexanone and adding a 3-halo-2-butanone compound, heat the reaction for a few hours and thereafter isolate a compound of formula (1)

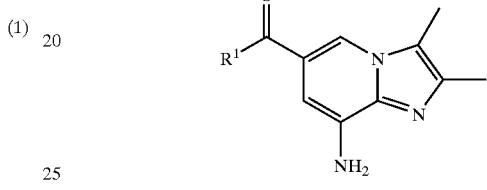

(1)

wherein $R^1$ is a $C_1$–$C_6$ alkoxy or $NH_2$ group, in high yields.

The amount of cyclohexanone is not crucial for carrying out the present invention, and can therefore in practical circumstances be adjusted according to needs and equipment used. It is also possible to mix cyclohexanone with inert solvents, such as ethers. Example of suitable inert solvents comprises, but is not limited, to tetrahydrofuran (THF). The amount of inert solvent can be up to around 50%, by volume, without causing a decrease in yield.

The amount of 3-halo-2-butanone compound is not critical for carrying out the present invention. It is for practical and economical reasons preferred to add 1.1 to 5 molar equivalents, preferably 1.1 to 2 equivalents. Example of suitable 3-halo-2-butanone compounds comprises, but is not limited, 3-bromo-2-butanone and 3-chloro-2-butanone, of which the latter is preferred.

Reaction temperatures and reaction times can be varied to meet the actual need. It is preferred to have a reaction temperature from 80° C. to 100° C. This reaction temperature gives a complete reaction within a few hours, e.g. 1 to 4 hours. Conversion is usually above 95% and the isolated yield is usually above 70%.

The starting material to be used in the present invention can be prepared as disclosed in WO 99/55706 or alternatively as is described below in Scheme 1.

Scheme 1

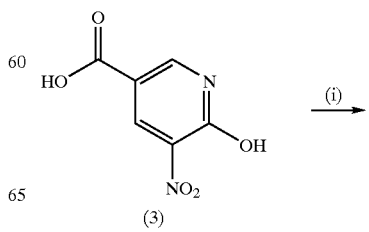

(3)

(i)

-continued

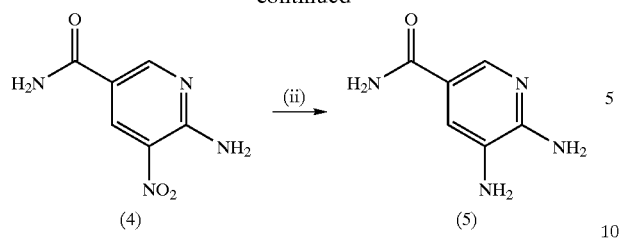

Step i

Compound (3) in Scheme 1 is treated with thionyl chloride, or any equivalent reagent, at elevated temperature in an appropriate solvent for a few hours to give the corresponding chloride compound. The reaction is performed using around 1 to 5 equivalents thionyl chloride, preferably 1 to 2.5 equivalents, in toluene at approximately 100° C. for 2 to 8 hours. The corresponding chloride compound is thereafter treated with 2 to 25 equivalents ammonia, preferably 3 to 12 equivalents, in the same solvent as above at approximately ambient temperature to give compound (4).

Step ii

Compound (4) in Scheme 1 is hydrogenated in an aqueous alcoholic solution using a catalyst to give compound (5). Example of suitable catalyst comprises, but is not limited, to palladium, ruthenium or mixtures thereof. Pd—Ru/C paste is the preferred catalyst. Examples of alcohols comprises, but is not limited to, methanol, ethanol and propanol, of which methanol is preferred.

The substituted imidazopyridine compound of formula (1),

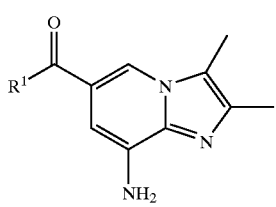

wherein $R^1$ is a $C_1$–$C_6$ alkoxy or $NH_2$ group, prepared according to the present invention can thereafter be used to prepare certain substituted imidazopyridine derivatives that are particularly effective as inhibitors of the gastrointestinal $H^+$, $K^+$-ATPase and thereby as inhibitors of gastric acid secretion.

Compounds of the Formula (1) can be reacted with a compound of the Formula (6)

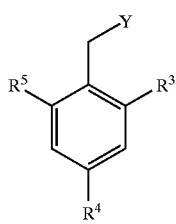

wherein $R^3$ is H, $C_1$–$C_6$ alkyl, hydroxylated $C_1$–$C_6$ alkyl or halogen; $R^4$ is H, $C_1$–$C_6$ alkyl, hydroxylated $C_1$–$C_6$ alkyl or halogen; $R^5$ is H, or halogen; and Y is a leaving group, such as a halide, tosyl or mesyl group, to give a compound of Formula (7).

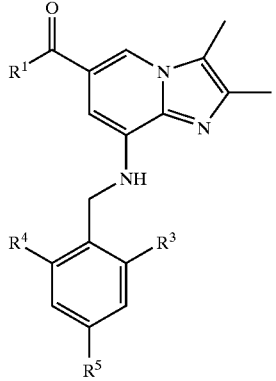

wherein $R^1$, $R^3$, $R^4$, and $R^5$ are as defined above. It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide, an alkali metal carbonate, such as potassium carbonate and sodium carbonate; or an organic amine, such as triethylamine.

Compounds of the Formula (7) wherein $R^1$ is $C_1$–$C_6$ alkoxy can thereafter be further reacted with an amino compound of the general Formula (8)

wherein $R^6$ and $R^7$ are the same or different and chosen from a group consisting of H, $C_1$–$C_6$ alkyl, hydroxylated $C_1$–$C_6$ alkyl, $C_1$–$C_6$ alkoxy-substituted $C_1$–$C_6$ alkyl, hydroxylated $C_1$–$C_6$ alkoxy-substituted $C_1$–$C_6$ alkyl, aryl, to give the corresponding amide compound.

$R^6$ and $R^7$ may together with the nitrogen atom to which they are attached, form a saturated or unsaturated ring optionally containing one or more further heteroatoms thereby forming e.g. morpholine, piperazine, pyrrolidine, or piperidine.

The reaction can be carried out by heating the reactants in the neat amino compound or dissolved in an inert solvent under standard conditions.

Alternatively can compounds of the Formula (7)

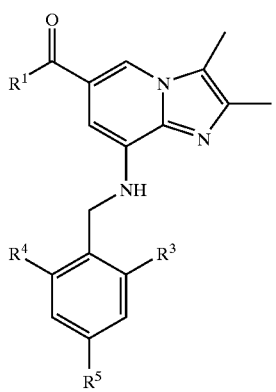

wherein R³, R⁴, and R⁵ are as defined above and R¹ is an NH₂ group, be hydrolyzed under standard conditions to the corresponding carboxylic acid compounds of Formula (9)

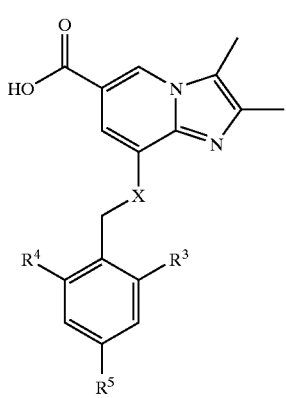
(9)

wherein R³, R⁴, and R⁵ are as defined above.

Compounds of the Formula (9) can thereafter be reacted with amino compounds of Formula (8)

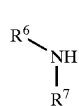
(8)

wherein R⁶ and R⁷ are as defined above, in the presence of a coupling reagent to give the corresponding amide compound. The reaction can be carried out in an inert solvent under standard conditions.

EXAMPLES

Example 1.1
Preparation of Bromobutanone

In a reactor, sodium bromide (84 kg) is suspended in dimethylformamide (125 l). 3-Chloro-2-butanone (85 kg) is added at 15° C.–30° C. Stirring is continued for 4 hours and then filtered: The filtercake is washed with cyclohexanone (38 l). The bromobutanone thereby prepared is ready to be used in the cyclisation step.

Example 1.2
Synthesis of Methyl 8-amino-2,3-dimethylimidazo[1,2-a] pyridine-6-carboxylate

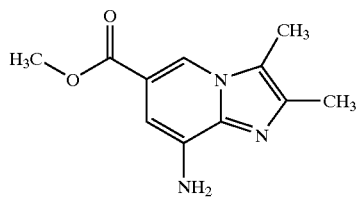

To a suspension of 5,6-diamino-nicotinic acid methyl ester (1 eq., 5.1 g) in cyclohexanone (50 ml) bromobutanone (1.2 equiv., 3.9 ml) was added over 10 min. The mixture was heated to 100° C. (inner temperature) and stirred 2.5 h at this temperature. The mixture was cooled to room temperature and the pale solid was filtered off and was washed with TBME (3×10 ml). Drying under reduced pressure at 45° C. Yield: 6.53 g (75%).

Example 1.3
Synthesis of Ethyl 8-amino-2,3-dimethylimidazo[1, 2-a] pyridine-6-carboxylate

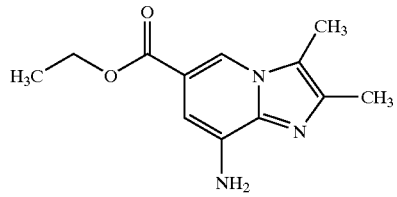

To a suspension of 5,6-diamino-nicotinic acid ethyl ester (1 eq., 5.0 g) in cyclohexanone (50 ml) bromobutanone (1.4 equiv., 5.95 g) was added over 15 min. The dark brown mixture was heated to 100° C. (inner temperature) and stirred 1.5 h at this temperature. The mixture was cooled to room temperature and the light brown solid was filtered off and was washed with TBME (20 ml). Drying under reduced pressure at 45° C. Yield: 5.06 g (65%).

Example 1.4
Synthesis of Isopropyl 8-amino-2,3-dimethylimidazo[1,2-a] pyridine-6-carboxylate

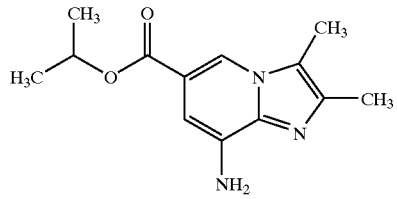

To a suspension of 5,6-diamino-nicotinic acid isopropyl ester (1 eq., 5.1 g) in cyclohexanone (50 ml) bromobutanone (1.2 equiv., 3.4 ml) was added over 10 min. The dark brown mixture was heated to 100° C. (inner temperature) and stirred 1.5 h at this temperature. The suspension was cooled to room temperature and the pale yellow solid was filtered off and was washed with TBME (3×10 ml). Drying under reduced pressure at 45° C. Yield: 6.0 g (74%).

Example 1.5
Synthesis of 8-amino-Z 3-dimethylimidazo[1,2-a]pyridine-6-carboxamide

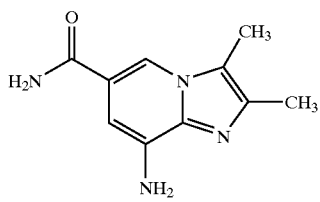

5,6-Diamino-nicotinamide (50 g, 0.313 mol (assay: 95.4%), 1.0 equiv.) was suspended in cyclohexanone (250 mL). The suspension was heated to 100° C. The filtrate (bromobutanone in cyclohexanone) was added at 100° C. over 1 h 10 min. Heating was continued for 3 h and the heating source was thereafter removed. The reaction mixture was allowed to cool to 20° C. and stirred at this temperature for another 2 h. The solid was filtered off, washed carefully with TBME (2×330 mL) and dried to yield 70.3 g of title compound. Yield: 70%.

Example 1.6
Synthesis of 8-amino-2,3-dimethylimidazo[1,2-a]pyridine-6-carboxamide

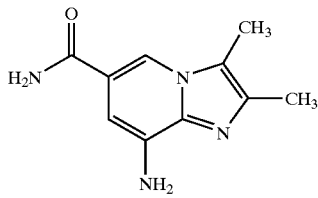

NaBr (27.0 g; 0.259 mol; 1.33 equiv) was suspended in cyclohexanone (220 mL) and 3-chloro-2-butanone (25.7 mL; 0.242 mol; 1.24 equiv) was added in one portion. The mixture was heated to 80° C. and stirred for 3 h. The mixture was cooled to 50° C., the white solid was filtered off and washed with cyclohexanone (60 mL). 5,6-Diamino-nicotinamide (30 g; 0.1946 mol; 1.0 equiv) was added to the filtrate and the mixture was heated to 100° C. for 4 h, after which 98% conversion was determined by HPLC. The reaction mixture was cooled to 20° C., stirring was continued for 2 h at 20° C. The solid was filtered off, washed with TBME (220 mL) and dried to yield 46.6 g of the title compound. Yield: 73%.

Example 1.7
Synthesis of 8-amino-2,3-dimethylimidazo[1,2-a]pyridine-6-carboxamide

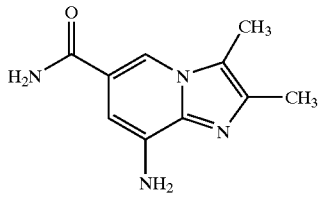

5,6-Diamino-nicotinamide (30.0 g; 0.183 mol; 1.0 equiv) was suspended in cyclohexanone (280 mL). 3-Bromo-2-butanone (24 mL; 0.22 mol; 1.2 equiv) was added and the mixture was heated for 4 h to 100° C. The reaction mixture was cooled to 20° C. and allowed to stir for another 2 h. The solid was filtered off, washed with TBME (200 mL) and dried to yield 48.4 g of the title compound. Yield: 78%.

Example 1.8
Synthesis of Methyl 2,3-dimethyl-8-(2,6-dimethylbenzylamino)-imidazo[1,2-a]pyridine-6-carboxylate

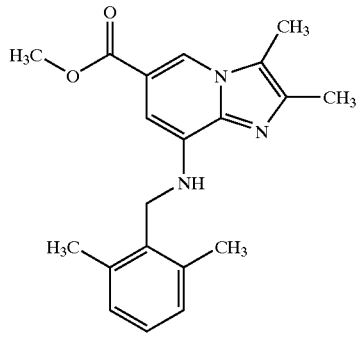

Methyl 8-amino-2,3-dimethylimidazo[1,2-a]pyridine-6-carboxylate (0.8 g, 3.6 mmol), 2,6-dimethylbenzylchloride (0.57 g, 3.7 mmol), sodium carbonate (1.0 g, 9.4 mmol) and a catalytic amount of potassium iodide were added to acetonitrile (10 ml) and were refluxed for 20 h. Following filtration, the salts were washed with methylene chloride and the solvents were evaporated under reduced pressure. The residue was purified by column chromatography on silica gel using methylene chloride: ethyl acetate (75:25) as eluent. The yellow residue was treated with hexane to give 0.23 g (19%) of the title product.

Example 1.9
Synthesis of Ethyl 2,3-dimethyl-8-(2-ethyl-6-methylbenzylamino)-imidazo[1,2-a]pyridine-6-carboxylate

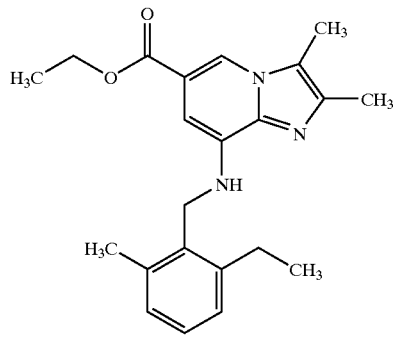

Ethyl 8-amino-2,3-dimethylimidazo[1,2-a]pyridine-6-carboxylate (0.7 g, 3.0 mmol), 2-ethyl-6-methylbenzylchloride (0.5 g, 3.0 mmol), sodium carbonate (0.64 g, 6.0 mmol) and a catalytic amount of potassium iodide were added to acetone (50 ml) and were refluxed for 20 h. Following filtration, the acetone was evaporated under reduced pressure to give an oil. The oily product was purified by column chromatography on silica gel using diethyl ether:petroleum ether (1:1) as eluent to give 0.12 g (9%) of the title product. $^1$H-NMR (500 MHz, CDCl$_3$): δ 1.25 (t, 3H), 1.5 (t, 3H), 2.35 (s, 3H), 2.42 (s, 3H), 2.44 (s, 3H), 2.75 (q, 2H), 4.45–4.5 (m, 4H), 4.9 (bs, 1H), 6.8 (s, 1H), 7.05–7.2 (m, 3H), 8.1 (s, 1H)

Example 1.10
Synthesis of 2,3-dimethyl-8-(2-ethyl-6-methylbenzylamino)-N-propyl-imidazo[1,2-a]pyridine-6-carboxamide

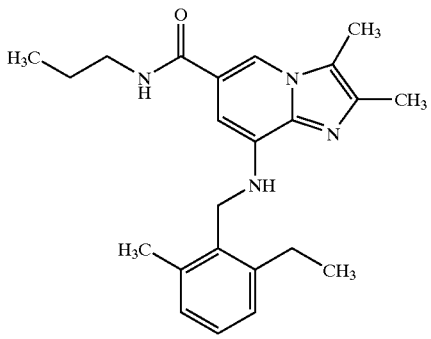

Ethyl 2,3-dimethyl-8-(2-ethyl-6-methylbenzylamino)-imidazo[1,2-a]pyridine-6-carboxylate (0.12 g, 0.33 mmol), propylamine (1.0 g, 17 mmol) and a catalytic amount of sodium cyanide were refluxed in methanol (20 ml) for 24 h. An additional amount of propylamine (1.0 g, 17 mmol) was added and the reaction mixture was refluxed for 24 h. The solvent was evaporated under reduced pressure and the residue was purified by column chromatography on silica gel using diethyl ether as eluent. Crystallization from diethyl ether gave 0.053 g (42%) of the title compound. $^1$H-NMR (300 MHz, CDCl$_3$): δ 1.0 (t, 3H), 1.2 (t, 3H), 1.65-1.75 (m, 2H), 2.3 (s, 3H), 2.35 (s, 3H), 2.38 (s, 3H), 2.7 (q, 2H), 3.4–3.5 (m, 2H), 4.35 (d, 2H), 4.9 (bs, 1H), 6.2 (bs, 1H), 6.35 (s, 1H), 7.0–7.2 (m, 4H), 7.85 (s, 1H).

Example 1.11

Synthesis of 2,3-dimethyl-8-(2-ethyl-6-methylbenzylamino)-imidazo[1,2-a]pyridine-6-carboxamide

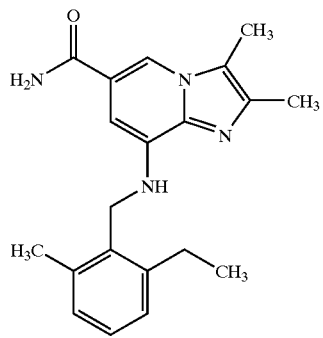

8-Amino-2,3-dimethylimidazo[1,2-a]pyridine-6-carboxamide (3.3 g, 16.2 mmol), 2-ethyl-6-methylbenzylchloride (2.73 g, 16.2 mmol), potassium carbonate (8.0 g, 58 mmol) and potassium iodide (1.1 g, 6.6 mmol) were added to acetone (150 ml) and refluxed for 20 h. An additional amount of 2-ethyl-6-methylbenzylchloride (1.0 g, 5.9 mmol) was added and the reaction mixture was refluxed for 7 h. Methylene chloride (60 ml) and methanol (30 ml) were added. The reaction mixture was filtered and the solvents were evaporated under reduced pressure. The residue was purified by column chromatography on silica gel using methylene chloride: methanol (100:7) as eluent. Crystallization from ethyl acetate gave 2.8 g (50%) of the title compound. $^1$H-NMR (300 MHz, CDCl$_3$): δ 1.2 (t, 3H), 2.34 (s, 3H), 2.36 (s, 3H), 2.38 (s, 3H), 2.7 (q, 2H), 4.4 (d, 2H), 4.9 (bs, 1H), 6.0 (bs, 2H), 6.45 (s, 1H), 2H), 6.45 (s, 1H), 7.0–7.2 (m, 3H), 7.9, (s, 1H).

Example 1.12

Synthesis of 2,3-dimethyl-8-(2-ethyl-6-methylbenzylamino)-imidazo[1,2-a]pyridine-6-carboxylic acid

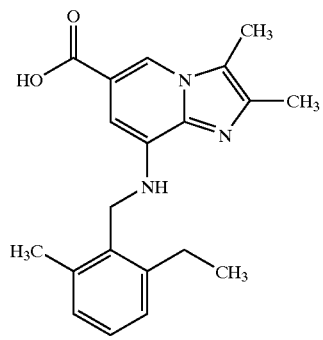

2,3-dimethyl-8-(2-ethyl-6-methylbenzylamino)-imidazo[1,2-a]pyridine-6-carboxamide mesylate (11.0 g, 0.025 mol) and sodium hydroxide (7.0 g, 0.17 mol) were solved in ethanol (95%) (120 ml) and was refluxed for 20 h. The solvent was evaporated under reduced pressure and to the residue was added water (50 ml). The pH was adjusted to 5 by addition of conc. HCl and acetic acid and the solid that precipitated was isolated by filtration, washed with water and acoetone, and dried to give 7.6 g (88%) of the title compound. $^1$H-NMR (500 MHz, DMSO-d$_6$): δ 1.15 (t, 3H), 2.26 (s, 3H), 2.34 (s, 3H), 2.39 (s, 3H), 2.69 (q, 2H), 4.38 (d, 2H), 5.2 (bs, 1H), 6.73 (s, 1H), 7.07–7.2 (m, 3H), 8.12 (s, 1H)

Example 1.13

Synthesis of 2,3-dimethyl-8-(2-ethyl-6-methylbenzylamino)-6-(morpholinocarbonyl)-imidazo[1,2-a]pyridine

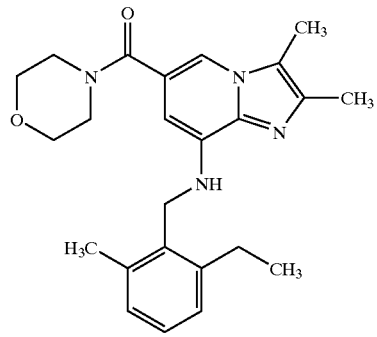

2,3-Dimethyl-8-(2-ethyl-6-methylbenzylamino)-imidazo[1,2-a]pyridine-6-carboxylic acid (0.15 g, 0.44 mmol) and o-Benzotriazol-1-yl-N,N,N',N'-Tetramethyluronium tetrafluoroborate (TBTU)(0.14 g, 0.44 mmol) were added to methylene chloride (10 ml). Morpholine (0.12 g, 1.4 mmol) was added and the reaction mixture was stirred at ambient temperature for 1.5 h. The reaction mixture was added to a column with silica gel and purification by chromatography using ethyl acetate:methylene chloride (1:1) as eluent gave 0.12 g (66%) of the desired product. $^1$H-NMR (300 MHz, CDCl$_3$): δ 1.2 (t, 3H), 2.32 (s, 3H), 2.35 (s, 3H), 2.37 (s, 3H), 2.7 (q, 2H), 3.7 (s, 8H), 4.35 (d, 2H), 4.95 (bs, 1H), 6.15 (s, 1H), 7.0–7.2 (m, 3H), 7.4 (s, 1H)

Example 1.14

Synthesis of (2-ethyl-6 methylbenzylamino)-N(2-(2-hydroxyethoxy)ethyl)-2,3-dimethylimidazo[1,2-a]pyridine-6-carboxamide

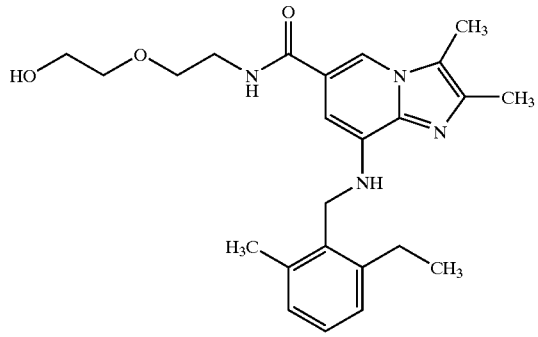

2,3-dimethyl-8-(2-ethyl-6-methylbenzylamino)-imidazo[1,2-a]pyridine-6-carboxylic acid (0.3 g, 0.88 mmol) and o-Benzotriazol-1-yl-N,N,N',N'-Tetramethyluronium tetrafluoroborate (TBTU)(0.29 g, 0.90 mmol) were added to methylene chloride (10 ml). 2-(2-aminoethoxy)ethanol (0.2 g, 1.9 mmol) was added and the reaction mixture was stirred at ambient temperature for 2 h. The solvent was evaporated under reduced pressure and the residue was purified by column chromatography on silica gel using methylene chloride:methanol (9:1) as eluent. Crystallization from diethyl ether gave 0.24 g (80%) of the desired product. $^1$H-NMR (500 MHz, CDCl$_3$): δ 1.25 (t, 3H), 2.25 (s, 3H), 2.3 (s, 3H), 2.35 (s, 3H), 2.75 (q, 2H), 3.4–3.45 (m, 21), 3.55–3.7 (m, 6H), 4.35 (d, 2H), 5.05 (t, 1H), 6.45 (s, 1H), 7.0–7.2 (m, 4H), 7.5 (s, 1H)

Example 1.15

Synthesis of Isopropyl 8-[(2,6-dimethylbenzyl)amino]-2,3-dimethylimidazo[1,2-a]pyridine-6-carboxylate

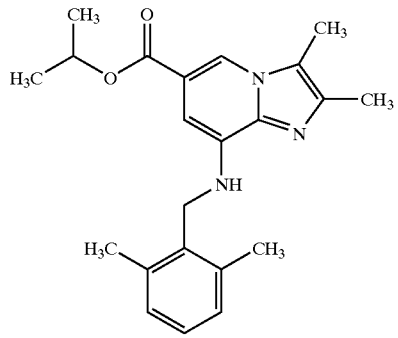

Isopropyl 8-amino-2,3-dimethylimidazo[1,2-a]pyridine-6-carboxylate (9.85 kg, 1.0 equiv., 29.71 mol) was suspended in isopropanol (59 L); NaI (0.6 equiv., 2.68 kg, 17.88 mol) and is K$_2$CO$_3$ (2.5 equiv, 10.29 kg, 74.48 mol) were added and the mixture was heated to about 70° C. 2,6-Dimethylbenzyl chloride (1.1 equiv, 5.22 kg, 32.77 mol) was dissolved in isopropanol (~60 L) and this solution was added to the reaction mixture. After the addition was complete, the temperature was kept at 60° C. for additional 1.5 hours. Additional K$_2$CO$_3$ was added (9.15 kg) and the resulting suspension was stirred for further 2 h at 60° C. Additional 2,6-dimethylbenzyl chloride (2.76 kg) in isopropanol (22L) was added slowly at an temperature of 60° C.; after the addition the reaction mixture was stirred for further 4 hours at this temperature. The suspension was diluted with water (124L), cooled, stirred and filtered. The filtercake was washed with water and then with cold isopropanol, dried under reduced pressure at 40° C. to give 11.37 kg wet material, yield: 90%.

Example 1.16

Synthesis of 8-[(2,6-dimethylbenzyl)amino]-N-(2-hydroxyethyl)-2,3-dimethylimidazo[1,2-a]pyridine-6-carboxamide

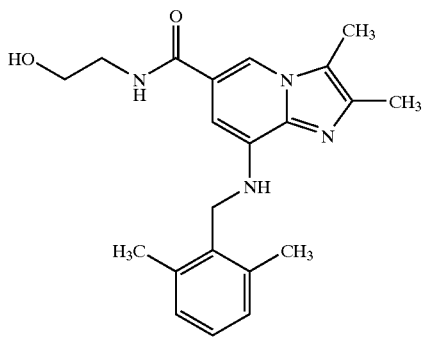

A reactor was charged with isopropyl 8-[(2,6-dimethylbenzyl)amino]-2,3-dimethylimidazo[1,2-a]pyridine-6-carboxylate (11.30 kg, 1 equiv., 27.02 mol) and THF (45 L), ethanolamine (18.97 kg, 11 equiv., 309.2 mol) was added at about 20° C. The suspension was heated to about 100° C. Some solvent was distilled off and then THF (35L) was added and the distillation was continued. The procedure of adding THF and distilling it off was repeated until complete conversion. To the suspension ethanol (140L) was added and the suspension was heated to reflux. To obtain a clear solution additional ethanol (13L) was added. The hot solution was filtered and then cooled. The white solid was filtered off, washed with ethanol and dried to yield the product as a white powder. (8271 g).

2. Preparation of Starting Materials

Example 2.1

Synthesis of 6-amino-5-nitro-nicotinamide 100 g of 6-hydroxy-5-nitro-nicotinic acid (0.54 mol; HPLC>98% area) was suspended in toluene (750 mL). DMF (1 mL, 0.013 mol, 0.024 equiv.) was added and the mixture was heated to 110° C. (inner temperature). Thionylchloride (99 mL, 2.5 equiv.) was added over 120 min. Heating was continued for 4 h at 110° C. The reaction mixture was concentrated to half the volume (400 mL of solvent were distilled off), and toluene (400 mL) was added.

This procedure was repeated once again (410 mL of toluene were distilled off and fresh toluene (410 mL) was added again). The solution was then cooled to 20° C. and slowly added to aqueous ammonia (25%, 440 mL, 12 equiv.) over 40 min. Precipitation started immediately. During the addition the temperature was maintained below 15° C. After the addition had been completed the reaction mixture was allowed to warm up to room temperature and stirring was continued for 16 h. The solid was filtered off, washed with water (500 mL), ethanol (250 mL), TBME (250 mL) and dried (50–10 mbar, 40° C. bath temperature, 16 h) to yield 91.3 g of the title compound (0.501 mol, 87%).

Example 2.2

Synthesis of 5,6-diamino-nicotinamide 44.5 g of 6-amino-5-nitro-nicotinamide (0.24 mol; HPLC: 93% area) were suspended in methanol/water 1:1 (500 mL), 5.0 g of catalyst [Pd(4%)-Ru(1%)/C paste (62% H$_2$O type: 485; Johnson Matthey); type: 485; Johnson Matthey] was added. Hydrogenation was carried out at 5 bar and 30° C. for 5 h. After completion the catalyst was filtered off and washed with methanol/water 1/1 (50 mL). 480 mL of the solvent was distilled off. The resulting suspension was cooled to 20° C. and filtered off. The solid was washed with methanol (20 mL) and TBME (30 mL). After drying (200-10 mbar; 40° C. bath temperature, 16 h) 27.3 g of the title compound (0.18 mol, 73%) were obtained.

Example 2.3

Synthesis of 5,6-diamino-nicotinamide 42.3 g of 6-amino-5-nitro-nicotinamide (0.23 mol, HPLC: 93% area) was suspended in methanol/water 1:1 (500 mL). 5.2 g of catalyst [Pd(5%)/C (57.8% H$_2$O); type: 39, Johnson Matthey] was added. Hydrogenation was carried out at 5 bar and 30° C. for 4 h. After completion the catalyst was filtered off and washed with methanol/water 1/1 (100 mL). 550 mL of the solvent was distilled off. The resulting suspension was cooled to 20° C. and filtered off. The solid was washed with methanol (20 mL) and TBME (30 mL). After drying (200-10 mbar; 40° C. bath temperature, 16 b) 28.5 g of the title compound (0.18 mol, 78%) was obtained.

What is claimed is:

1. A process for preparing a substituted imidazopyridine compound of formula (1)

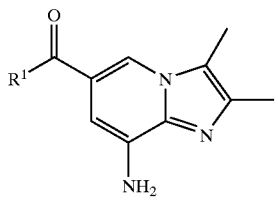
(1)

wherein R¹ is $C_1$–$C_6$ alkoxy or $NH_2$,
comprising the step of reacting a compound of formula (2)

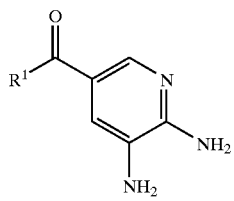
(2)

with a 3-halo-2-butanone compound in cyclohexanone.

2. The process according to claim 1, wherein the 3-halo-2-butanone compound is 3-bromo-2-butanone or 3-chloro-2-butanone.

3. The process according to claim 1 or 2, wherein the amount of the 3-halo-2-butanone compound is in the range of 1.1 to 5 molar equivalents.

4. The process according to claim 1, wherein the reaction temperature is in the range of 80° C. to 100° C.

5. The process according to claim 1, wherein the cyclohexanone is diluted with an inert solvent.

6. The process according to claim 1, wherein R¹ is $C_1$–$C_6$ alkoxy.

7. The process according to claim 1, wherein R¹ is $NH_2$.

8. The process according to claim 1, wherein the compound of formula (2) is prepared by a process comprising the step of hydrogenating a compound of formula (4)

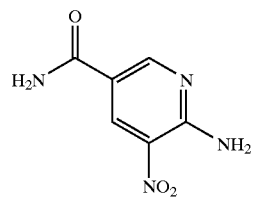
(4)

in an aqueous alcoholic solution using a catalyst.

9. The process according to claim 8, wherein the catalyst is a Pd—Ru/C paste.

10. The process according to claim 8 or 9, wherein the compound of formula (4) is prepared by a process comprising the step of reacting a compound of formula (3)

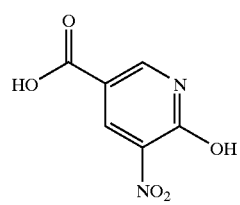
(3)

with thionyl chloride to give a corresponding chloride compound, which is thereafter treated with ammonia to yield the compound of formula (4).

* * * * *